(12) United States Patent
Davidsen et al.

(10) Patent No.: US 9,730,677 B2
(45) Date of Patent: Aug. 15, 2017

(54) MATRIX ULTRASOUND PROBE WITH PASSIVE HEAT DISSIPATION

(75) Inventors: Richard Edward Davidsen, Andover, MA (US); Steven Russell Freeman, Seattle, WA (US); Bernard Joseph Savord, Andover, MA (US)

(73) Assignee: KONINKLIJKE PHILIPS ELECTRONICS N.V., Eindhoven (NL)

( * ) Notice: Subject to any disclaimer, the term of this patent is extended or adjusted under 35 U.S.C. 154(b) by 218 days.

(21) Appl. No.: 14/113,384

(22) PCT Filed: May 11, 2012

(86) PCT No.: PCT/IB2012/052364
§ 371 (c)(1),
(2), (4) Date: Oct. 23, 2013

(87) PCT Pub. No.: WO2012/156886
PCT Pub. Date: Nov. 22, 2012

(65) Prior Publication Data
US 2014/0058270 A1 Feb. 27, 2014

Related U.S. Application Data

(60) Provisional application No. 61/486,796, filed on May 17, 2011.

(51) Int. Cl.
*A61B 8/00* (2006.01)
*G01S 15/89* (2006.01)
*G01S 7/52* (2006.01)

(52) U.S. Cl.
CPC ........... *A61B 8/546* (2013.01); *A61B 8/4209* (2013.01); *A61B 8/4444* (2013.01);
(Continued)

(58) Field of Classification Search
None
See application file for complete search history.

(56) References Cited

U.S. PATENT DOCUMENTS 5,213,103 A * 5/1993 Martin .................... A61B 8/00
600/443
5,545,942 A 8/1996 Jaster et al.
(Continued)

FOREIGN PATENT DOCUMENTS

EP 1652476 A2 5/2006
EP 1671588 A1 6/2006
(Continued)

*Primary Examiner* — Patricia Park

(57) ABSTRACT

A matrix array ultrasound probe passively dissipates heat developed by the matrix array transducer and beamformer ASIC away from the distal end of the probe. The heat developed in the transducer stack is coupled to a metallic frame inside the handle of probe. A metallic heatspreader is thermally coupled to the probe frame to convey heat away from the frame. The heatspreader surrounds the inside of the probe handle and has an outer surface which is thermally coupled to the inner surface of the probe housing. Heat is thereby coupled evenly from the heatspreader into the housing without the development of hotspots in the housing which could be uncomfortable to the hand of the sonographer.

17 Claims, 4 Drawing Sheets

(52) U.S. Cl.
CPC .......... *A61B 8/4494* (2013.01); *G01S 7/5208* (2013.01); *G01S 7/52096* (2013.01); *G01S 15/8925* (2013.01)

(56) References Cited

U.S. PATENT DOCUMENTS

| | | | |
|---|---|---|---|
| 5,560,362 A | 10/1996 | Sliwa et al. | |
| 5,721,463 A | 2/1998 | Snyder | |
| 5,961,465 A | 10/1999 | Kelly et al. | |
| 2004/0241447 A1* | 12/2004 | Fukushima | C04B 41/009 428/408 |
| 2005/0075573 A1 | 4/2005 | Park et al. | |
| 2006/0186765 A1* | 8/2006 | Hashimoto | A61B 8/546 310/334 |
| 2008/0188755 A1* | 8/2008 | Hart | A61B 8/00 600/459 |
| 2008/0194954 A1* | 8/2008 | Unger | A61B 17/22012 600/439 |
| 2008/0194963 A1* | 8/2008 | Randall | A61B 8/00 600/459 |
| 2009/0227910 A1 | 9/2009 | Pedersen et al. | |
| 2010/0168576 A1 | 7/2010 | Poland | |
| 2010/0331702 A1* | 12/2010 | Hongou | A61B 8/14 600/459 |
| 2011/0230767 A1 | 9/2011 | Miyajima | |
| 2012/0143060 A1 | 6/2012 | Weekamp | |

FOREIGN PATENT DOCUMENTS

| | | | |
|---|---|---|---|
| EP | 2366430 A1 | | 9/2011 |
| JP | H02203846 A | | 8/1990 |
| JP | 2004329495 A | | 11/2004 |
| JP | 2006025892 A | | 2/2006 |
| JP | 2006204552 A | | 8/2006 |
| JP | 2007158468 A | | 6/2007 |
| WO | 9701768 | | 1/1997 |
| WO | WO2008/146203 | * | 12/2008 |
| WO | 2009083896 A | | 7/2009 |
| WO | 2010150539 A1 | | 12/2010 |

* cited by examiner

_US 9,730,677 B2_

MATRIX ULTRASOUND PROBE WITH PASSIVE HEAT DISSIPATION

This application is the U.S. National Phase application under U.S.C. §371 of International Application No. PCT/2012/052364, filed May 11, 2012, which claims the benefit of U.S. Provisional Patent Application No. 61/486,796 filed May 17, 2011. These applications are hereby incorporated by reference herein.

This invention relates to medical diagnostic systems and, in particular, to matrix array transducer probes with passive heat dissipation.

Conventional one dimensional (1D) array transducer probes for two dimensional (2D) imaging are actuated by transmit drive circuitry located in the system mainframe. The probe cable is plugged into the system mainframe and the transducer elements of the array at the probe face are driven for transmission by the drive circuitry in the mainframe system. While the heat generated by piezoelectric actuation of the transducer elements must be dissipated by the probe, the heat generated by the high voltage drive circuitry in the system mainframe can be relatively easily dissipated by the system. However, solid-state 3D imaging probes have a two dimensional matrix of transducer elements numbering in the thousands, and a cable with thousands of coaxial drive signal conductors is impractical. Consequently a beamformer ASIC (microbeamformer) is employed in the probe with integrated drive circuitry and receive circuitry for the transducer elements in the probe itself. The beamformer ASIC controls and performs at least part of the transmit and receive beamforming so that only a relatively few signal path conductors are needed in the cable, enabling the use of a practical, thin cable for the 3D imaging probe.

With the transmit beamforming ASIC and drive circuitry in the probe, the heat generated by this circuitry must now be dissipated from the probe, not the system mainframe. Since the beamforming ASIC is attached directly behind the transducer array, the heat of the transducer stack and ASIC is now at the front of the probe, just behind the lens which contacts the patient. Various approaches have been taken in the past to dissipate heat from the front of an ultrasound probe. One approach shown in U.S. Pat. No. 5,213,103 (Martin et al.) is to use a heatsink extending from the transducer at the front of the probe to the cable braid at the back. Heat is conducted away from the transducer by the heatsink and into the cable braid, from which it dissipates through the cable and the probe housing. Martin et al. are only transporting the heat from the piezoelectric transducer without the drive circuitry, as the drive circuitry for the Martin et al. probe is presumably in the system mainframe. A more aggressive approach to cooling is to use active cooling as described in U.S. Pat. No. 5,560,362 (Sliwa, Jr. et al.) or a thermoelectric cooler as described in US Pat. pub. no. US 2008/0188755 (Hart). Active cooling with a coolant requires the necessary space and apparatus to circulate the coolant as well as the hazard of coolant leaks, and both approaches complicate the component complexity and spacing inside the probe. What is needed is a passive cooling technique which is more effective than that of Martin et al. and without the complications of the active cooling approaches. It is further desirable for such a passive cooling technique to avoid the development of hotspots in the probe which can concentrate heat at a specific point or points of the probe case and hence into the hand of the probe user.

In accordance with the principles of the present invention, a matrix array ultrasound probe is described which uses passive heat dissipation to dissipate heat generated by a matrix array transducer and ASIC. The heat generated by these elements is conducted to a heat spreader which distributes the heat through a surface area beneath the probe housing. The distribution of heat by the heat spreader prevents the buildup of hotspots at a particular point or points of the handle portion of the probe housing. The distributed heat is then dissipated through the probe housing and probe cable.

Figure 1:
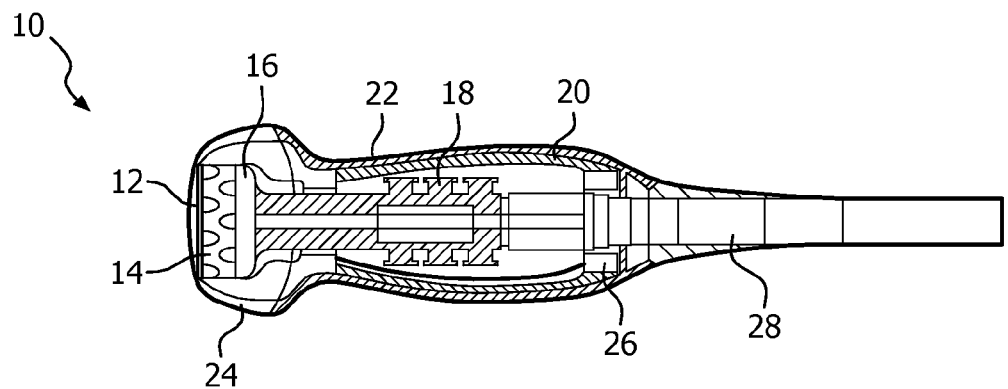
FIG. 1 illustrates a first cross-sectional view of matrix array ultrasound probe constructed in accordance with the principles of the present invention.

Referring first to FIG. 1, a matrix array ultrasound probe 10 constructed in accordance with the principles of the present invention is shown in cross-section. The probe 10 has an outer case 22 which forms the handle portion of the probe which is held by a sonographer when using the probe. The distal end of the probe is enclosed by a nosepiece housing 24. Behind a lens 36 covering the distal end is a matrix array transducer backed by an ASIC, both of which are indicated at 12. The integrated circuitry of the ASIC controls transmission by the transducer elements and performs both transmit and receive beamforming of signals transmitted and received by the array. An interposer can be employed if desired to couple the elements of the transducer array to the circuitry of the ASIC. One such interposer is described in international patent pub. WO 2009/083896 (Weekamp et al.), for instance. Behind the matrix array transducer and ASIC is a graphite backing block 14 which attenuates acoustic reverberations from the back of the matrix array and conducts heat developed in the matrix array and ASIC away from the distal end of the probe. Further details of the graphite backing block may be found in co-pending U.S. patent application No. 61/453,690, filed Mar. 17, 2011. An aluminum or magnesium probe frame 16 is in thermally conductive contact with the back of the graphite backing block to conduct heat further away from the distal end of the probe. The frame 16 also mounts electrical components of the probe which themselves are mounted on two printed circuit boards and occupy the space inside the probe indicated by 18. At the back of the probe and extending from the proximal end of the probe is a probe cable 28. The cable 28 is clamped to the rear of the frame by a clamp 26.

Figure 2:
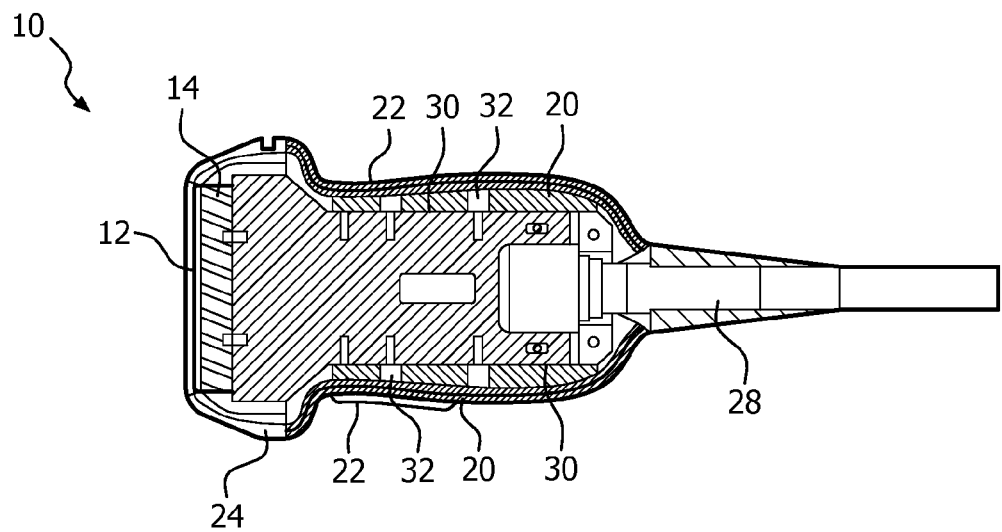
FIG. 2 illustrates a second cross-sectional view, orthogonal to FIG. 1, of a matrix array probe constructed in accordance with the principles of the present invention.
Figure 3:
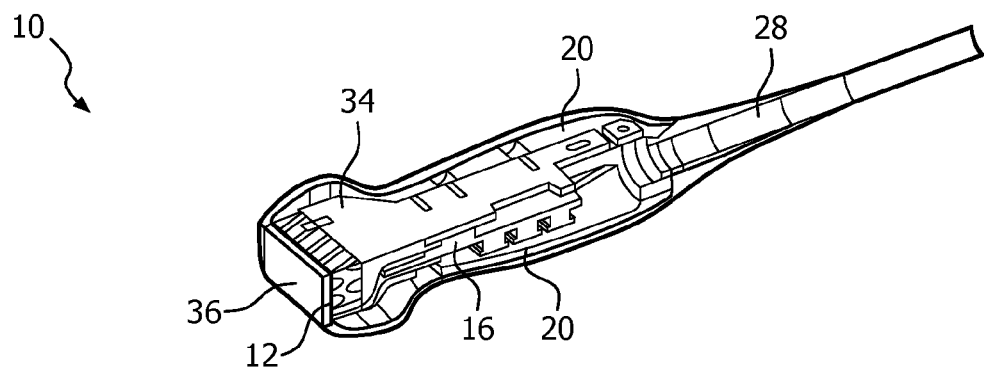
FIG. 3 is a quarter-section cross sectional view of the matrix array probe of FIGS. 1 and 2.

Surrounding the frame 16 in the handle portion of the probe is a heatspreader 20. The heatspreader is in thermally conductive contact with the two sides of the frame 16 as shown in FIG. 2. This thermal contact is promoted by a thermal gasket such as one formed with thermally conductive tape or a thermal compound (putty) where the heatspreader 20 contacts the sides of the frame 16 at 30. The heatspreader 20 is held in place against the frame 16 and its thermal coupling by screws at 32. FIG. 3 is a one-quarter cross-sectional view of the probe of FIGS. 1 and 2 showing a printed circuit board 34 on top of the frame 16 and the heatspreader 20 surrounding the frame 16 and printed circuit boards in the handle portion of the probe.

Figure 4:
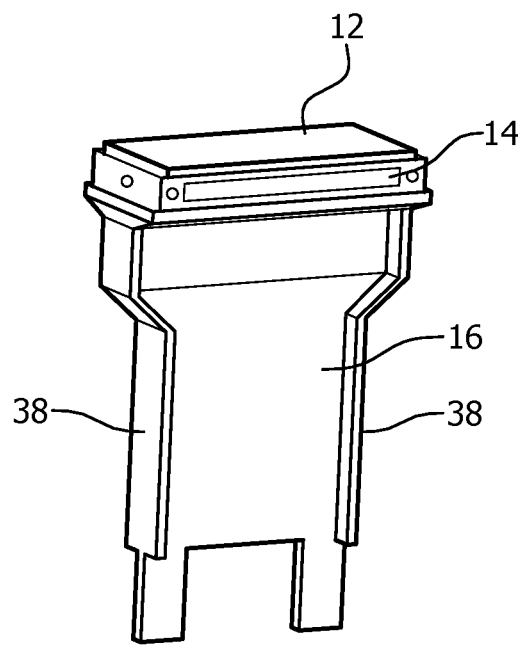
FIG. 4 illustrates a matrix array transducer stack, ASIC, and backing block mounted on a thermally conductive probe frame.

FIG. 4 is a perspective view of one embodiment of the frame 16 with the graphite backing block 14 and matrix array transducer and ASIC 12 mounted on top of the frame and in thermally conductive contact with the frame. In this embodiment there are flanges 38 on the sides of the frame 16 to which the heatspreader is attached for efficient heat conduction from the frame to the heatspreader.

Figure 5:
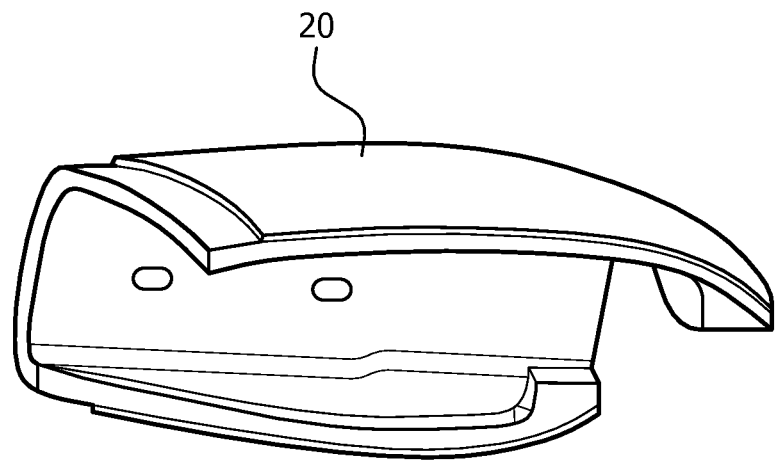
FIG. 5 is a perspective view of one-half of a heat spreader for a matrix array probe.

FIG. 5 illustrates one implementation of a heatspreader 20. In this implementation the heatspreader is formed as two clamshell halves which fit together at diagonally located edges. The half illustrated in the view of FIG. 5 surrounds the inside of the handle portion of the housing 22 on the back and top, and its mating half surrounds the front and bottom of the handle interior. Visible in this view are two holes through which screws are inserted to fasten the heatspreader to one side of the frame 16.

Figure 7:
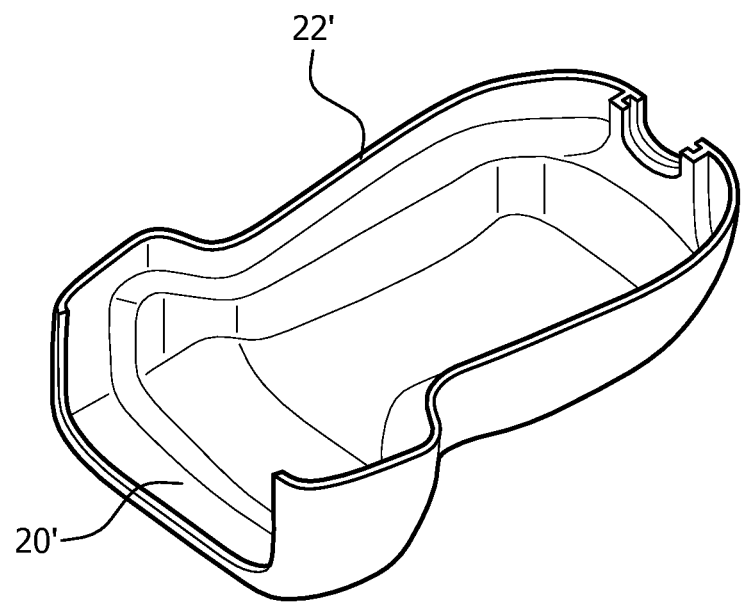
FIG. 7 illustrates a probe housing which is molded around one-half of a heat spreader.

FIG. 7 illustrates another implementation of the heatspreader in which the housing 22 is molded around the metal heatspreader. In this implementation the handle portion 22 and the nosepiece 24 are molded as a single housing 22' which is formed around the heatspreader 20' so that the heatspreader 20' surrounds not only the volume inside the handle, but also extends forward to surround the transducer stack in the distal end of the housing. The heatspreader 20' will thus be in direct thermally conductive contact with the graphite backing block which carries heat away from the matrix array and ASIC 12. Heat in the distal end of the probe will therefore be carried to the rear of the probe and dissipated by both the probe frame 16 and the heatspreader 20'.

Figure 6:
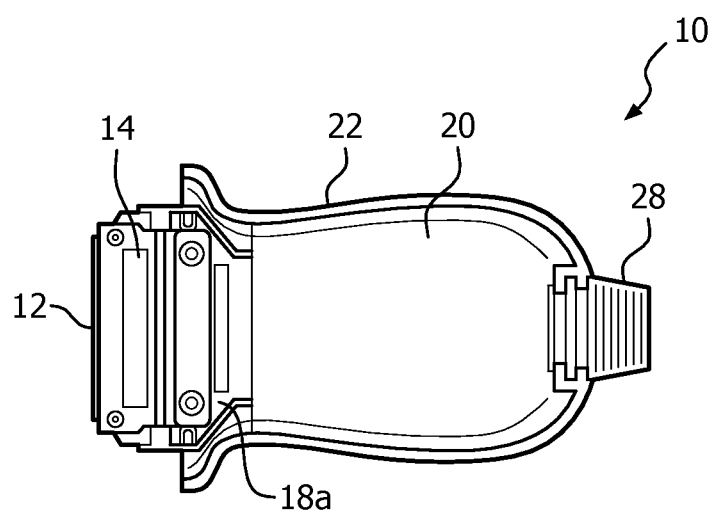
FIG. 6 illustrates the matrix array probe of the previous drawings assembled with one-half of the probe housing removed.

FIG. 6 is a plan view of an assembled probe 10 of the present invention with the nosepiece and half of the housing 22 removed. This view shows the heatspreader 20 completely enclosing the frame 16 and printed circuit boards inside the handle portion of the housing 22. The heatspreader 20 conducts heat over its entire area, avoiding the buildup of hotspots at particular points inside the housing. The development of such hotspots can be felt by the hand of the sonographer using the probe and, while they may not be sufficient to pose a danger, they can make use of the probe uncomfortable. A benefit of the present invention is that heat is distributed throughout the heatspreader inside the housing and individual hotspots will not develop. The heat conducted by the heatspreader is conducted from the outer surface of the heatspreader 20 to the inner surface of the housing 22 from which it dissipates through the housing and into the air. To promote the transfer of heat into the housing 22 from the heatspreader 20, a layer of thermal putty may be spread between the heatspreader and the housing, carrying heat into the housing over its entire inner surface area and further preventing the buildup of hotspots in the housing.

Figure 8:
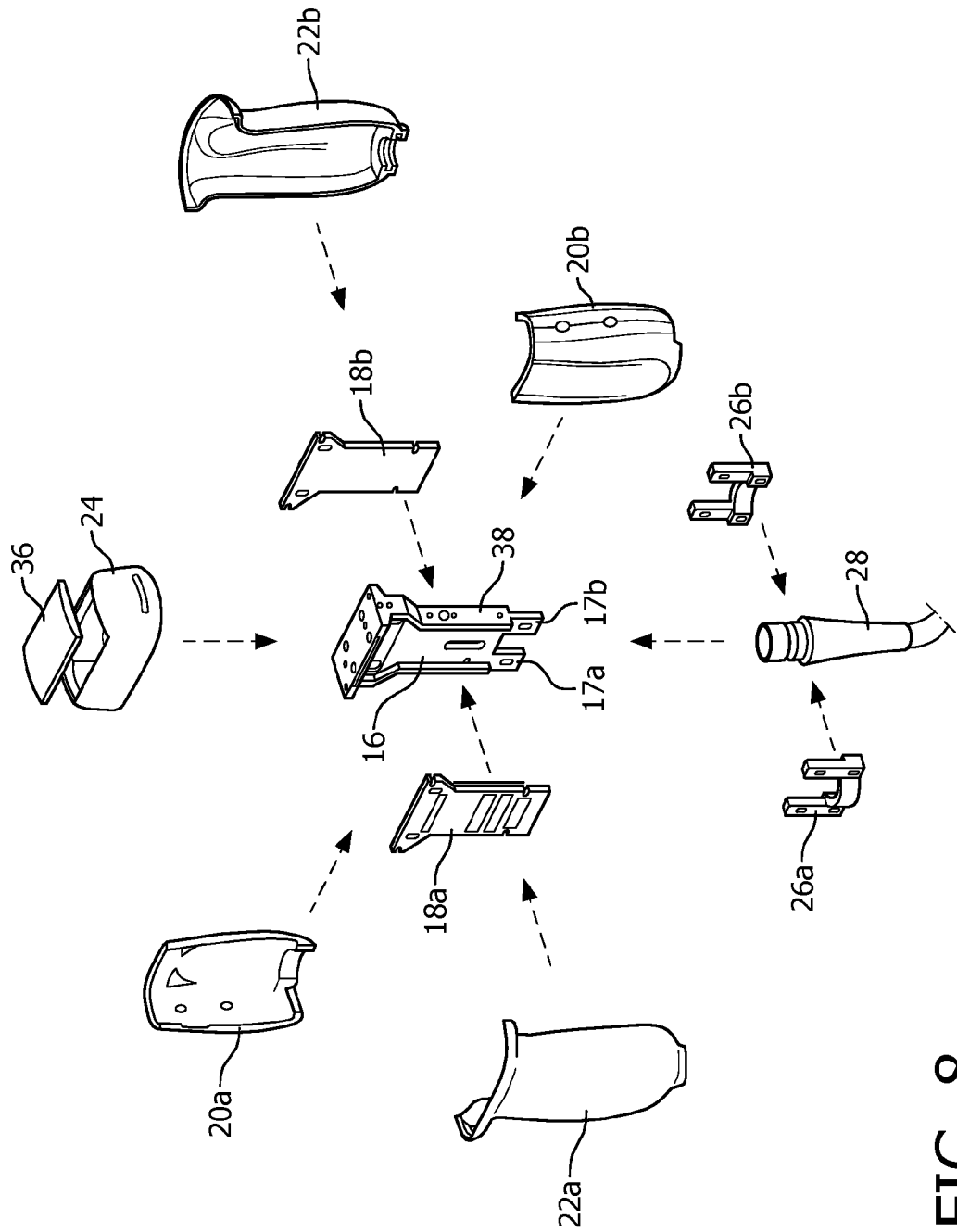
FIG. 8 is an exploded assembly drawing of the major component parts of the matrix array probe of FIGS. 1-6.

FIG. 8 is an exploded view showing the assembly of a probe 10 of the present invention including many of the components described above. The transducer stack, including the matrix array transducer and beamformer ASIC 12 and the graphite backing block 14 (not shown in this drawing) are fastened to the top of the probe frame 16 as shown in previous drawings. Printed circuit boards 18a and 18b are fastened to opposite sides of the frame 16. Wires from the cable 28 are connected to connectors on the printed circuit boards and a clamp 26a and 26b is clamped around the strain relief and braid of the cable 28 and the clamp is also clamed to two rails 17a and 17b extending from the proximal end of the frame 16. This coupling of the proximal end of the frame 16 to the cable braid promotes the transfer of heat from the frame into the cable braid and away from the probe. A thermal gasket or thermal putty covers the surfaces of the flanges 38 of the frame 16 and the two halves 20a and 20b of the heatspreader are fastened to the flange sides of the frame 16 with screws. The nosepiece 24 and lens 36 are placed on the distal end of the assembly over the transducer stack. The outer surface of the assembled heatspreader (or the inner surfaces of the housing halves) are coated with thermal putty and the housing is put in place around and in contact with the heatspreader and thermal putty with the seams of the housing and nosepiece sealed to prevent fluid ingress. The assembled probe is now ready for final testing and delivery to a user.

What is claimed is:

1. An ultrasonic transducer array probe comprising:
a transducer stack having an array of transducer elements coupled to an application specific integrated circuit (ASIC) for a transducer array;
a thermally conductive frame which is thermally coupled to the transducer stack;
a housing comprising a handle portion, the housing enclosing at least a portion of the thermally conductive frame that extends into the handle portion; and
a thermally conductive heatspreader which is thermally coupled to the frame and surrounds at least a portion of the frame that extends into the handle portion, wherein the heatspreader includes an outer surface area which aligns with and is thermally coupled to an inner surface area of the housing, and wherein the heatspreader comprises two clamshell halves disposed in the handle portion which surround a perimeter of the frame within the handle portion.

2. The ultrasonic transducer array probe of claim 1, wherein the array of transducer elements further comprises a two dimensional matrix array of transducer elements.

3. The ultrasonic transducer array probe of claim 2, wherein the ASIC further comprises a beamformer ASIC which at least partially beamforms transmit beams from the matrix array and echo signal received by elements of the matrix array.

4. The ultrasonic transducer array probe of claim 1, further comprising a thermally conductive backing block located between the ASIC and the frame.

5. The ultrasonic transducer array probe of claim 1, further comprising a thermal gasket or thermal putty which provides thermal coupling between the frame and the heatspreader.

6. The ultrasonic transducer array probe of claim 5, wherein the frame has side flanges, and wherein the heatspreader is fastened in thermally conductive contact with the side flanges of the frame.

7. The ultrasonic transducer array probe of claim 6, wherein the heatspreader is screwed or bolted to the side flanges of the frame.

8. The ultrasonic transducer array probe of claim 1, further comprising a thermal gasket or thermal putty which provides thermal coupling between the heatspreader and the housing.

9. The ultrasonic transducer array probe of claim 1, further comprising a thermally conductive backing block located between the ASIC and the frame, wherein the heatspreader is directly thermally coupled to the backing block.

10. The ultrasonic transducer array probe of claim 1, further comprising a printed circuit board fastened to the frame.

11. The ultrasonic transducer array probe of claim 1, further comprising a probe cable having a metallic braid, wherein the frame is further thermally coupled to the metallic braid of the cable.

12. The ultrasonic transducer array probe of claim 1, wherein the heatspreader is made of aluminum or magnesium.

13. The ultrasonic transducer array probe of claim 12, wherein the frame is made of aluminum or magnesium.

14. The ultrasonic transducer array probe of claim 1, wherein at least the handle portion of the housing is molded around at least a portion of the heatspreader to form a one-piece unit.

15. The ultrasonic transducer array probe of claim 1, further comprising flanges that extend along each side of the frame into the handle portion of the housing.

16. The ultrasonic transducer array probe of claim 1, wherein the two clamshell halves fit together at diagonally located edges.

17. The ultrasonic transducer array probe of claim 1, wherein the heatspreader extends into a nosepiece portion of the housing and surrounds at least a portion of the transducer stack.

\* \* \* \* \*